US007002122B2

United States Patent
Eves, II et al.

(10) Patent No.: US 7,002,122 B2
(45) Date of Patent: Feb. 21, 2006

(54) CHOKE ASSEMBLY FOR CONTINUOUS CONVEYOR MICROWAVE OVEN

(75) Inventors: E. Eugene Eves, II, Westford, MA (US); Bruce Secovich, Hudson, NH (US)

(73) Assignee: The Ferrite Company, Inc., Nashua, NH (US)

( * ) Notice: Subject to any disclaimer, the term of this patent is extended or adjusted under 35 U.S.C. 154(b) by 0 days.

(21) Appl. No.: 10/965,271

(22) Filed: Oct. 14, 2004

(65) Prior Publication Data

US 2005/0092741 A1    May 5, 2005

Related U.S. Application Data

(60) Provisional application No. 60/514,457, filed on Oct. 24, 2003.

(51) Int. Cl.
*H05B 6/76* (2006.01)
*H05B 6/78* (2006.01)

(52) U.S. Cl. .................... 219/699; 219/700; 219/738; 219/756; 174/35 GC

(58) Field of Classification Search ........ 219/698–701, 219/693, 695, 736–738, 756; 174/35 R, 174/35 GC
See application file for complete search history.

(56) References Cited

U.S. PATENT DOCUMENTS

| 2,627,571 A | * | 2/1953 | Hiehle et al. | 219/699 |
| 3,177,333 A | * | 4/1965 | Lamb | 219/693 |
| 3,474,209 A | * | 10/1969 | Parker | 219/696 |
| 4,227,063 A | * | 10/1980 | Edgar et al. | 219/699 |
| 4,401,873 A | * | 8/1983 | Berggren et al. | 219/693 |
| 4,999,469 A | * | 3/1991 | Dudley et al. | 219/693 |

* cited by examiner

*Primary Examiner*—Philip H. Leung
(74) *Attorney, Agent, or Firm*—Hamilton, Brook, Smith & Reynolds, P.C.

(57) ABSTRACT

A continuous feed microwave applicator having a choke formed along a longitudinal gap. A conveyor may be fit to run along the length of the applicator, within the gap.

7 Claims, 4 Drawing Sheets

CHOKE ASSEMBLY FOR CONTINUOUS CONVEYOR MICROWAVE OVEN

RELATED APPLICATION(S)

This application claims the benefit of U.S. Provisional Application No. 60/514,457, filed on Oct. 24, 2003. The entire teachings of the above application are incorporated herein by reference.

BACKGROUND OF THE INVENTION

Commercial food preparation operations typically involve cooking, drying and/or browning of items. It is often necessary to apply these processes to large quantities of food articles in the shortest possible time, and this has lead to the use of continuous feed microwave ovens of several types.

One such microwave oven makes use of an elongated, single mode microwave energy applicator. The single mode applicator is designed from an electromagnetic standpoint to be a waveguide that applies microwave energy in a shape that is optimized depending upon the shape of the product being cooked. For example, if the product being cooked is relatively square in cross-section, the applicator may itself be designed as an elongated, tapered rectangular cavity that is several feet long.

Such an applicator is, by necessity, left open on both ends so that food articles to be cooked may travel on a conveyor which travels inside the waveguide. With food portion sizes appropriate for heating using an applicator of this design, the product entrance and exit may be constructed using well known techniques to prevent microwave leakage. For example, the entrance and exit openings are typically limited in size to be something less than the propagating waveguide dimension, which in turn depends upon the wavelength of the microwave energy. Thus, for microwave applicators designed for operating in the 900 Megahertz (MHz) region, as long as openings are no more than about 6 inches or so in each dimension, energy will be contained.

However, the small dimensions necessary in construction of such an applicator pose several problems.

First, there is no direct access available to the interior of the rectangular waveguide for easy cleaning. While such applicators have been assembled from component pieces, and typically bolted together, disassembly of such a unit can be quite time consuming. Since there can be no uninterrupted opening of more than about six inches, bolts or other fasteners are typically placed at a spacing which is no longer than that.

Second, it is often preferred that a so-called endless conveyor belt be used that has no breaks in it. However, there is typically no easy way of removing an endless conveyor belt from such an applicator, since this again requires disassembly of the applicator via removal of the fasteners.

A third difficulty arises from the fact that there must be sufficient clearance between the edges of the belt and the interior walls of the applicator so that the belt may freely run along. However, there is a tendency for small food particles to fall between the belt edges and the applicator wall. This causes additional maintenance problems, further exacerbated by the difficulty in obtaining access to the interior of the applicator in the first place, and then having to remove the belt to clean out these small food particles.

SUMMARY OF THE INVENTION

The present invention is a continuous feed microwave applicator assembly, such as may be used for cooking food products. The applicator consists of an upper body portion and a lower body section. The upper and lower body sections are supported in a fixed, spatial relationship so that a gap is formed between them, along a longitudinal axis thereof. So that the applicator may be made sufficiently long enough, a choke assembly is placed along either side of the gap between the applicator sections, to prevent microwave energy from leaking out of the applicator. The choke assembly, which is preferable sealed to prevent food particles from entering, allows the applicator to be arbitrarily long.

A lift mechanism is preferably used to support the lower section. This permits the lower section to be moved down and away from the upper section, providing open and easy access to the interior of the applicator for cleaning.

A frame is also used to support a continuous conveyor belt in a generally horizontal orientation. In operation, the conveyor runs through the gap formed between the upper and lower applicator body sections.

In a preferred embodiment, the conveyor belt may be wider than the applicator sections. This allows the ends of the belt to extend beyond the applicator, so that no space exists for food particles to collect between the belt and the applicator walls.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF A PREFERRED EMBODIMENT

Figure 1:
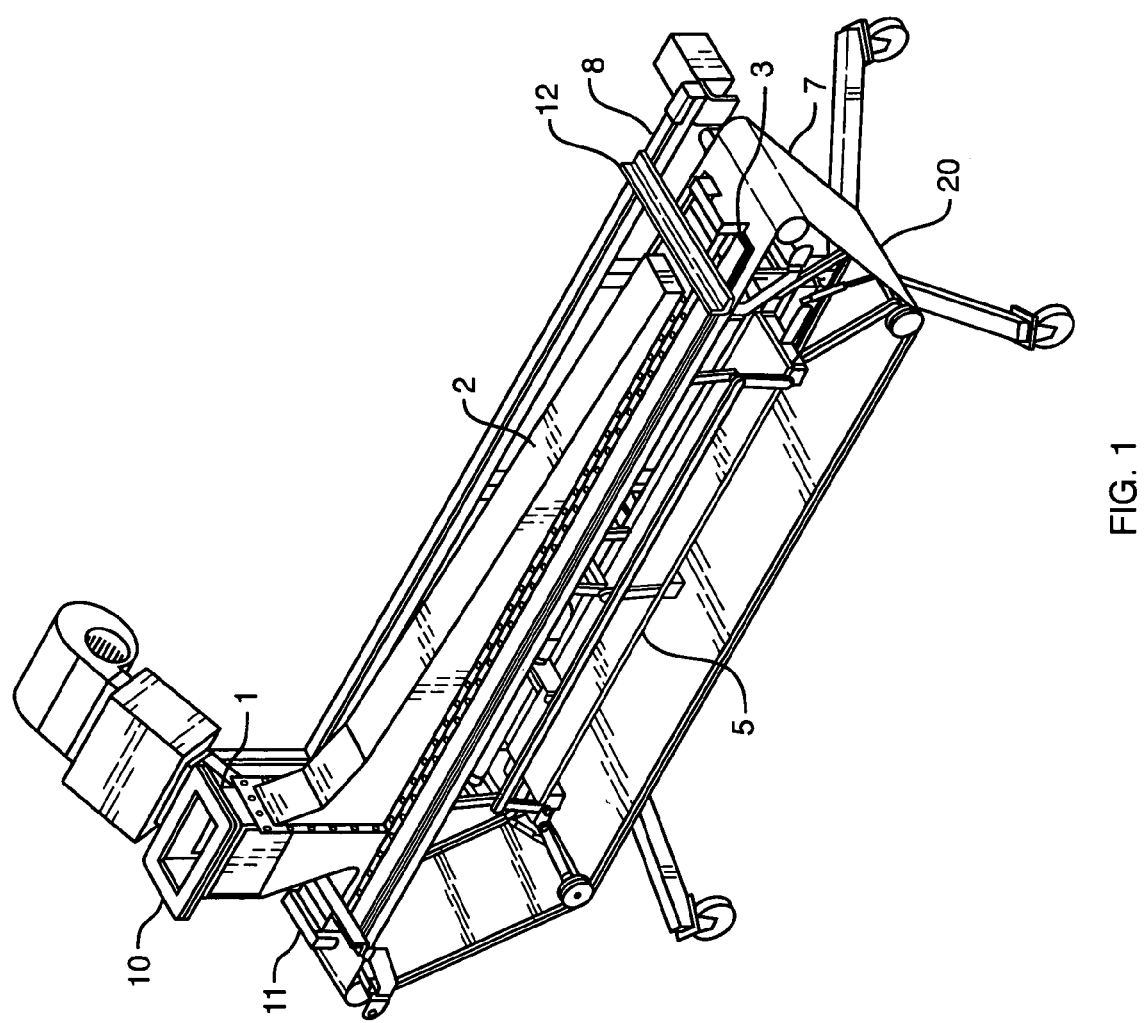
FIG. 1 is a perspective view of a microwave oven assembly.

FIG. 1 is a perspective view of a microwave applicator 1 according to the present invention. A microwave energy source (not shown) generates microwave energy to be feed to an input waveguide section 10. Waveguide section 10 then feeds microwave energy to an applicator body 1 serving as an oven. The applicator body 1 is open at both an inlet end 11 and outlet end 12. This permits food products to travel on a conveyor 20 while being cooked. As shown in the drawing, the conveyor 20 consists of a continuous belt 7 wrapped around a belt frame 8 and consists of suitable drive mechanisms, tensioners pulleys, and the like. In the preferred embodiment, the conveyor is a continuous belt of material such as Teflon™ or other material suitable for repeated use in commercial heating apparatus.

The body of the applicator 1 generally has an elongated but tapering shape starting from the inlet end 11 and tapering to the outlet end 12. The taper of the applicator 1 is chosen to provide for desired uniform distribution of microwave energy to the product as the product moves along the conveyor from the inlet 11 to the outlet 12. The gradually deceasing, rectangular cavity shape actually results in uniform application of energy as the product moves from the inlet towards the outlet.

While the applicator 1 is shown mounted on casters 18 should be understood that the same apparatus could be permanently mounted on a stand or other fixed platform as well The applicator 1 consists of an upper section 2 and lower section 6. As will be understood shortly a lift mechanism 5 permits the lower section 6 to be moved downward and away from the upper section 2. This permits easy access for cleaning the interior of the applicator 1.

Figure 2A:
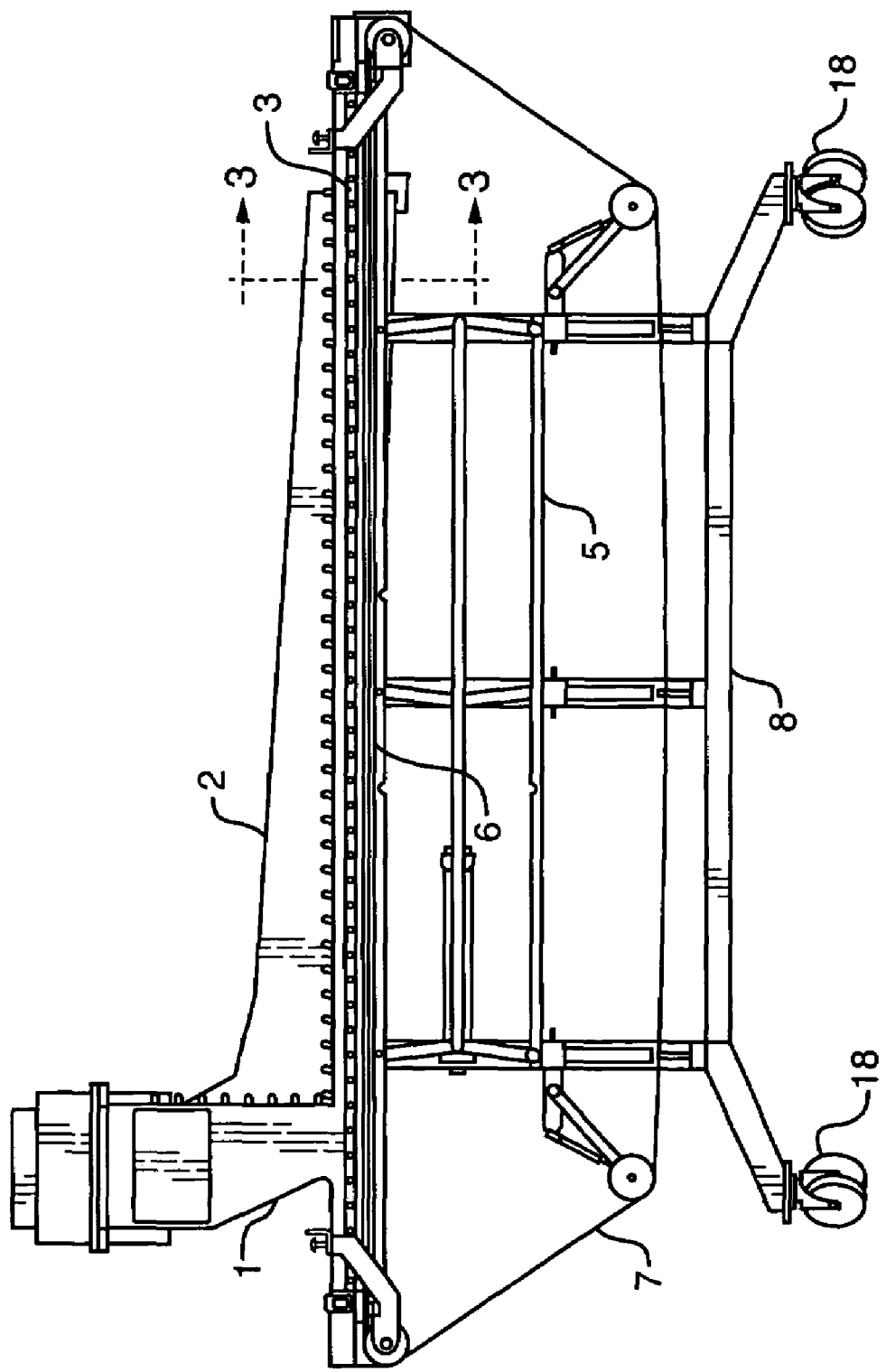
FIG. 2A shows the assembly in a cross-sectional view with the frame supporting the applicator in the closed position.

In FIG. 2A, the applicator 1 is shown in a side view with the upper portion 2 and lower portion 6 more readily seen. The applicator upper 2 and lower 6 portions provide a split or space along the body of the applicator 1. This provides a place for the belt 7 to run. In fact, the belt 7 is generally wider than the applicator 1 itself so that the outer edges of the belt 7 actually protrude beyond the edges of the applicator 1.

Figure 2B:
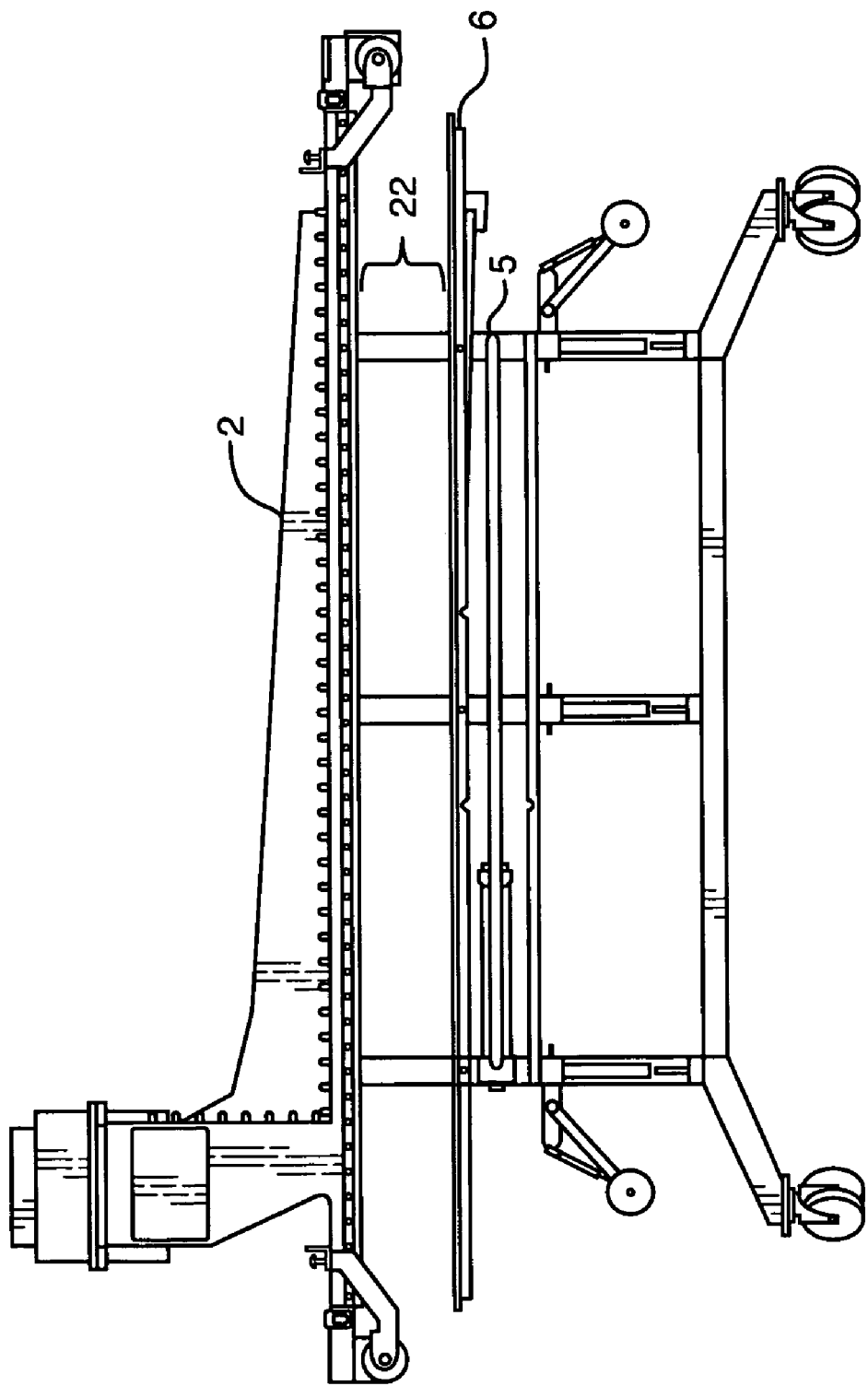
FIG. 2B shows the applicator in an open position such that it may be accessed for cleaning.

A lift 5 is utilized to permit lowering the applicator lower section 6 down and away from the applicator upper section 2. This is shown more particularly in FIG. 2B, where the lift 5 has been arranged in the downward position. While the belt 7 is not shown in this drawing it should be understood that the belt 7 would remain in position adjacent the upper portion 2, and the lift 5 operates only to adjust the position of the applicator lower section 6. In this position, a larger space 22 is formed between the upper 2 and lower 6 sections of the applicator 1, and it is possible to now clean the interior of the applicator. The lift 5 may be operated by compressed air, electric motor, by hand, or other convenient operating mechanism.

Figure 3:
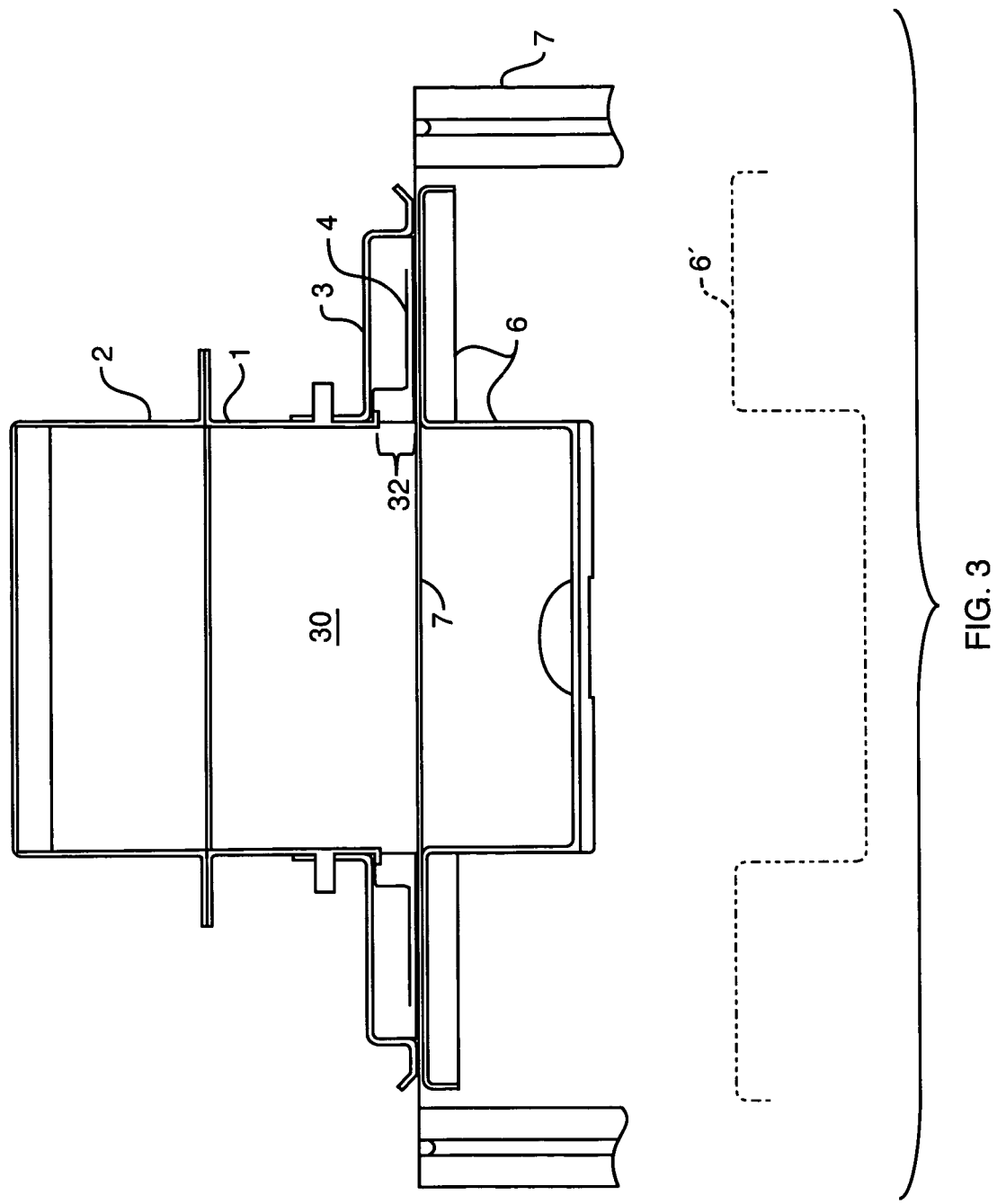
FIG. 3 is a cross-sectional view of the applicator showing how the conveyor belt runs through an opening formed between upper and lower applicator body sections, and the position of the choke.

FIG. 3 is a cross-sectional view taken along section lines A—A of FIG. 2A. Food product to be cooked travels into space 30 formed in the center more or less of the applicator body 1. Here the orientation of the belt 7 and how it fits in the gap formed between the applicator upper 2 and applicator lower 6 can be seen. A choke is formed of a choke body 3 and choke fingers 4. Choke body 3, as shown, is a flange formed on either side of the applicator body 1. Within the choke body 3, choke fingers 4 are placed. Choke fingers 4 are of a suitable choke material. The choke fingers 4 may be a covered with a continuous sheet of material such as teflon or silicone rubber, may be interdigitated fingers, an array of pin chokes or other suitable arrangements known to prevent microwave energy escaping through a gap.

A gap 32 is thus formed between the applicator body 1 and applicator lower portion 6 so that the belt 7 may travel therethrough. However, the choke 3 and especially the choke fingers 4 prevent the escape of microwave energy through the gap 32 while at the same time allowing the belt 7 to freely move so that product may travel through the applicator 1.

When cleaning is desired it can be understood how that the applicator lower portion 6 is placed in the position indicated by 6', to provide access to the interior of the applicator 1.

While this invention has been particularly shown and described with references to preferred embodiments thereof, it will be understood by those skilled in the art that various changes in form and details may be made therein without departing from the scope of the invention encompassed by the appended claims.

What is claimed is:

1. A continuous feed microwave applicator comprising:
   an applicator main body adapted to receive microwave energy from a microwave waveguide; the applicator main body further comprising:
   an applicator upper section;
   an applicator lower section; and
   a radio frequency choke arranged along a gap formed between the upper and lower applicator sections;
   a conveyor, positioned between the applicator upper and lower sections; and
   a lift mechanism, for moving the applicator lower section downwards and away from the conveyor, to permit access to an anterior portion of the applicator lower section.

2. An apparatus as in claim 1 wherein said conveyor additionally comprises a conveyor belt, positioned between the applicator upper and lower sections.

3. An apparatus as in claim 1 where the applicator section is an elongated section running substantially the length of the conveyor.

4. An applicator as in claim 3 wherein the upper applicator section tapers from a larger opening at an inlet point to a smaller opening at an outlet point.

5. An apparatus as in claim 1 wherein the lift mechanism moves the lower section a distance sufficiently away from the conveyor to permit access for cleaning of an interior portion of the lower applicator portion.

6. An apparatus as in claim 1 wherein the distance is sufficient to permit cleaning by hand.

7. An apparatus as in claim 1 wherein the lower applicator has a generally U-shaped rectangular cross section with an open side positioned facing the upper applicator section and conveyor.

* * * * *